United States Patent [19]

Tolentino

[11] Patent Number: 4,558,111

[45] Date of Patent: Dec. 10, 1985

[54] METHOD FOR PREPARING ACRYLIC FUNCTIONAL HALOSILANES AND HALOSILOXANES

[75] Inventor: Luisito A. Tolentino, Ballston Lake, N.Y.

[73] Assignee: General Electric Company, Waterford, N.Y.

[21] Appl. No.: 678,321

[22] Filed: Dec. 5, 1984

[51] Int. Cl.[4] .............................................. C08G 77/04
[52] U.S. Cl. .................................... 528/26; 528/32; 556/440
[58] Field of Search ...................... 528/26, 32; 556/440

[56] References Cited

U.S. PATENT DOCUMENTS 3,878,263  4/1975  Martin .................................... 528/37
4,201,808  5/1980  Cully et al. .......................... 525/479

Primary Examiner—Melvyn I. Marquis
Attorney, Agent, or Firm—Gary L. Loser

[57] ABSTRACT

The instant invention provides a method for making acrylate-functional halosilanes or halosiloxanes comprising reacting an organic acrylate and a halosilane or halosiloxane having at least one silicon-bonded hydrogen atom in the presence of a hydrosilation catalyst and an amount of inhibitor effective for inhibiting the thermal free radical polymerization of said organic acrylate. Acrylate-functional halosilanes and halosiloxanes prepared in accordance with the present method are also provided.

10 Claims, No Drawings

METHOD FOR PREPARING ACRYLIC FUNCTIONAL HALOSILANES AND HALOSILOXANES

BACKGROUND OF THE INVENTION

The present invention relates to methods for making acrylic-functional silicone compositions. More particularly, the present invention relates to methods for making acrylic-functional silanes and siloxanes which employ novel inhibitors to prevent thermal free radical polymerization of the acrylic-functional reactants.

Ultraviolet light curable silicone compositions have gained widespread acceptance in many fields, for instance as release compositions for use with pressure sensitive adhesives. One reason for this success is that ultraviolet light curable compositions overcome many of the disadvantages of solvent-based systems such as the need for energy intensive ovens and solvent-recovery apparatus.

A variety of methods for preparing ultraviolet light curable silicone compositions are disclosed in the prior art.

Ohto et al., U.S. Pat. No. 3,865,588, teaches the addition reaction between (i) a compound having an unsaturated radical represented by the general formula

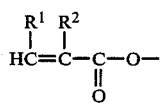

where $R^1$ is a hydrogen atom, phenyl radical, or a halogen substituted phenyl radial, and $R^2$ is a hydrogen atom or a methyl radical and also having an aliphatic unsaturated bond, and (ii) a silane represented by the general formula

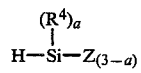

where $R^4$ is a monovalent hydrocarbon radical or a halogen substituted monovalent hydrocarbon radical having from 1 to 10 carbon atoms, Z is a halogen atom, an acetoxy radical, a hydroxyl radical or an alkoxy radical having from 1 to 4 carbon atoms, and a is a number representing 0 or 1, in the presence of a catalyst such as chloroplatinic acid. Ohto et al. also teach that the temperature of the reaction system can be raised in order to accelerate the reaction, however, in such case it is preferable to add some thermal polymerization inhibitor such as quinones, e.g., hydroquinone or benzoquinone, amine salts or hydrazine salts. Reference 8 of Ohto et al. discloses that 115 parts of methylhydrogendichlorosilane, 149 parts of monomethyltrichlorosilane, 211 parts of monophenyltrichlorosilane and 516 parts of dimethyldichlorosilane were added dropwise to a mixture of 1000 parts of toluene, 100 parts of methanol, and 5000 parts of water, which mixture was kept stirring at 5°-10° C. The reaction system was then washed until it's pH became 7.0, and then toluene was distilled from the system until the siloxane concentration was 50 percent. Subsequently a mixture of 138 parts of allyl methacrylate, 0.2 part of a 2 percent isopropanol solution of chloroplatinic acid and 0.5 part hydroquinone was added. When the addition was over the mixture was heated for ten hours at which time there was obtained a polymerizable silicone compound having a pour point of 48° C. Reference 8 thus illustrates that it is necessary to hydrolyze and alkoxylate the halosilane before effecting acrylation.

Martin, U.S. Pat. No. 3,878,263, discloses that acrylate-functional silanes and siloxanes may be prepared by the addition of a compound of the formula

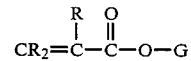

where R is a hydrogen atom or a $C_{1-12}$ monovalent hydrocarbon radical, and G is an unsaturated radical such as vinyl, allyl, methallyl, or butenyl, with a compound of the formula

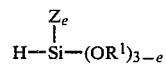

where $R^1$ is a hydrogen atom or a monovalent hydrocarbon radical, e is a number from 0 to 2, inclusive, and Z is selected from the class consisting of $R^1$, $OR^1$, and $OSi(R^2)_3$, where $R^2$ is a monovalent hydrocarbon radical, halogenated monovalent hydrocarbon radical or a cyanoalkyl radical. According to Martin, the reaction preferably is carried out in the presence of a polymerization inhibitor for acrylic acid or methacrylic acid, such as hydroquinone or N,N'-diphenylphenylene diamine. Again the artisan is taught that only alkoxy-functional silanes can be acrylated.

Tanaka, U.S. Pat. No. 4,139,548, discloses the preparation of methyldi(trimethylsiloxy)silylpropylglycerolmethacrylate by reacting methyldi(trimethylsiloxy)-silylpropyl(oxypropylene oxide) with methacrylic acid in the presence of a catalyst. In order to prevent the polymerization of methacrylic acid, it is desirable to carry out the reaction in the presence of a polymerization inhibitor such as hydroquinone, hydroquinone monomethyl ether or sulfur.

Cully et al., U.S. Pat. No. 4,201,808, discloses that radiation curable compositions having acrylic functionality can be stabilized against premature polymerization during storage by the addition of a conventional polymerization inhibitor such as hydroquinone, monomethyl ether of hydroquinone, phenothiazine, di-t-butyl paracresol, etc. in concentrations on the order of 0.1 weight percent or less.

Careful consideration of the foregoing disclosures reveals that in each instance the polymerization inhibitor was employed in a system free of chloride.

The present applicant determined that it would be desirable to effect acrylation of chlorosilanes, thus eliminating, the need to first alkoxylate the silane before reacting with an acrylate-containing compound, for example, as described in Ohto et al, U.S. Pat. No. 3,865.588, or Martin, U.S. Pat. No. 3,878,263. Accordingly, there was prepared a reaction mass of

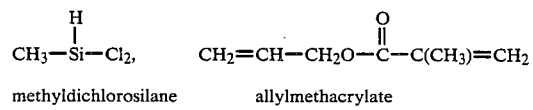

methyldichlorosilane     allylmethacrylate and an amount of platinum catalyst effective for promoting the reaction of these compounds. In order to prevent the thermal free radical polymerization of allylmethacrylate there was added a hydroquinone inhibitor. It was found that hydroquinone compounds are not effective for inhibiting the thermal free radical polymerization of the organic acrylate in the presence of chloride-containing compounds such as halosilanes.

SUMMARY OF THE INVENTION

It is an object of the present invention to provide a method for reacting a halosilane or halosiloxane with an organic acrylate so as to obtain a silane or siloxane having both chloro and acrylic functionality and which silane or siloxane can be hydrolyzed and/or condensed so as to provide an acrylic-functional polysiloxane.

It is another object of the present invention to provide a method for reacting a halosilane or halosiloxane and an organic acrylate which does not require that the silane or siloxane be alkoxylated before acrylation is effected.

It is still another object of the present invention to provide an inhibitor effective for preventing thermal free radical polymerization of acrylic compounds in the presence of halide-containing compounds.

In accordance with a preferred embodiment of the present invention there is provided a method for making acrylate-functional silanes or siloxanes by the addition of a compound of the formula

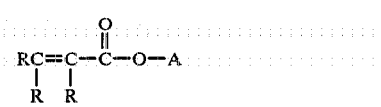

where the R's may be the same or different and represent hydrogen atoms or monovalent substituted or unsubstituted hydrocarbon radicals having from 1 to 12 carbon atoms, and A is an unsaturated radical such as vinyl, allyl, methallyl or butenyl and the like; with a compound of the formula

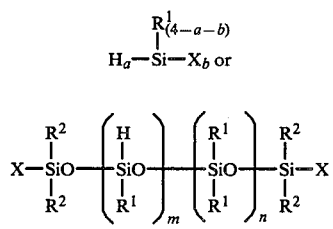

where $R^1$ is independently selected from the group consisting of monovalent substituted or unsubstituted hydrocarbon radicals having from 1 to 12 carbon atoms and monovalent substituted or unsubstituted hydrocarbonoxy radicals having from 1 to 12 carbon atoms, $R^2$ is hydrogen or $R^1$, X is a halogen, a equals 1, 2, or 3, b equals 1, 2 or 3, the sum of a plus b equals 2 to 4, inclusive, m and n are equal to or greater than 0, provided that if m is 0, at least one $R^2$ is H; in the presence of a hydrosilation catalyst and an amount of inhibitor selected from the group consisting of phenothiazine, phenanthroline, thiazole, 2-mercaptobenzothiazole, 2,4-dimethylthiazole and 2-benzimidazolethiol, effective for inhibiting the thermal free radical polymerization of said compound of the formula

DESCRIPTION OF THE INVENTION

In its broadest aspect, the present invention provides a method for making an acrylate-functional silane or siloxane comprising reacting an organic acrylate and a halosilane or halosiloxane having silicon-bonded hydrogen atoms in the presence of a hydrosilation catalyst and an amount of inhibitor effective for inhibiting the thermal free radical polymerization of said organic acrylate.

In a preferred embodiment the present invention provides a method for making acrylate-functional silanes or siloxanes comprising reacting a compound of the formula

 (I)

with a compound of the formula

 (II)

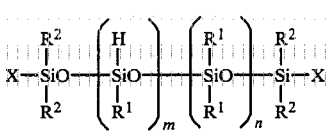 (III)

in the presence of a hydrosilation catalyst and an amount of inhibitor selected from the group consisting of phenothiazine, phenanthroline, thiazole, 2-mercaptobenzothiazole, 2,4-dimethylthiazole, and 2-benzimidazolethiol and the like, effective for preventing the thermal free radical polymerization of the said compound of the formula

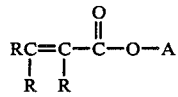

where A is an alkenyl radical having from 2 to about 6 carbon atoms, R is, independently, a hydrogen atom or monovalent substituted or unsubstituted hydrocarbon radical having from 1 to 12 carbon atoms, $R^1$ is selected from the group consisting of monovalent substituted or unsubstituted hydrocarbon radicals having from 1 to 12 carbon atoms and monovalent substituted or unsubstituted hydrocarbonoxy radicals having from 1 to 12 carbon atoms, $R^2$ is hydrogen or $R^1$, X is a halogen atom, a equals 1, 2 or 3, b equals 1, 2 or 3, the sum of a and b equals 2 to 4, inclusive, m and n are equal to zero or a positive integer with the proviso that if m is zero, at least one $R^2$ is hydrogen.

The above reaction can be illustrated as follows:

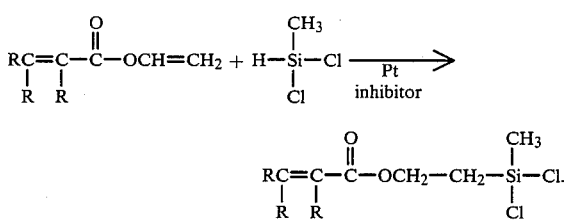

The acrylate functional halosilanes and halosiloxanes of the present invention can then be further reacted by methods known in the art to provide, for example, alkoxy or silanol endstopped polydiorganosiloxanes which are curable by exposing said polydiorganosiloxane to an effective amount of ultraviolet radiation or by heating in the presence of a free radical type catalyst.

In the present application the terms acrylic-functional, acrylate-functional and the like are synonomous and generally refer to compounds having present the functional group

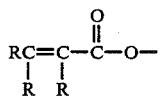

where R is as previously defined.

Among the radicals, in addition to hydrogen atoms, which R represents, are alkyl radicals such as methyl, ethyl, propyl and butyl; cycloalkyl radicals such as cyclopentyl, cyclohexyl and cycloheptyl; mononuclear and binuclear aryl radicals such as phenyl and naphthyl; aralkyl radicals such as benzyl, phenylethyl, and phenylpropyl; and alkaryl radicals such as tolyl, xylyl and ethylphenyl. Preferably R is a hydrogen atom, methyl radical or mixture thereof.

In formula I, A is an aliphatic unsaturated radical such as vinyl, allyl, methallyl, butenyl or other radical which will react with a silicon-bonded hydrogen atom in the presence of a hydrosilation catalyst. Preferably A is vinyl, allyl or methallyl.

Illustrative of compounds within the scope of Formula I are vinyl acrylate, allyl acrylate, vinyl cinnamate, allyl cinnamate, methallylcinnamate, vinyl methacrylate, allyl methacrylate, methallyl methacrylate. Preferably the compound of Formula I is allyl methacrylate. Of course, a mixture of compounds within the scope of Formula I can be employed.

Among the radicals within the scope of $R^1$ of Formula II and Formula III are alkyl radicals such as methyl, ethyl, propyl and butyl; alkoxy radicals such as methoxy, ethoxy, propoxy and butoxy, and any other radicals as defined hereinabove for R. Preferably $R^1$ is hydrogen or methyl. $R^2$ is an $R^1$ radical or hydrogen.

In Formula II and Formula III, X is a halogen atom such as fluorine, chlorine, bromine or iodine and most preferably is chlorine. The artisan will appreciate that the number of halogen atoms bonded to silicon in the silane of Formula II determines whether the resultant siloxy unit will be monofunctional, difunctional, trifunctional, or tetrafunctional.

Hydrosilation catalysts effective for promoting the reaction of the A radical of the compound of Formula I with the silicon-bonded hydrogen atom of the silane or siloxane of Formula II are well known in the art. The hydrosilation catalysts effective for practicing the present invention include all of the well known platinum and rhodium catalysts, for example, as described in U.S. Pat. Nos. 3,159,601 and 3,159,662 to Ashby, U.S. Pat. No. 3,220,970 to Lamoreaux, U.S. Pat. No. 3,814,730 to Karstedt and U.S. Pat. No. 3,516,946 to Modic. All of the foregoing patents relating to hydrosilation catalysts are incorporated by reference into the instant disclosure. In place of platinum and rhodium it is possible to employ other noble metals such as ruthenium, palladium, osmium and irridium, as the basis of the hydrosilation catalyst.

Quite unexpectedly quinones such as hydroquinone and benzoquinone were found to be ineffective for inhibiting the thermal free radical polymerization of compounds defined by Formula I in the presence of compounds having the structure set forth in Formula II and Formula III.

Accordingly, there is provided an inhibitor for preventing the thermal free radical polymerization of compounds of the formula

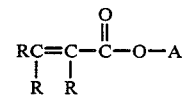

in the presence of a compound having the formula

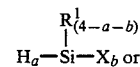

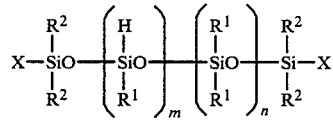

where $R^1$, $R^2$, X, a, b, m and n are as previously defined, which is selected from the group consisting of phenothiazine, phenanthroline, thiazole, 2-mercaptobenzothiazole, 2,4-dimethylthiazole and 2-benzimidazolethiol.

While not wishing to be bound by a particular theory, it is believed that quinones are ineffective as an inhibitor in the process of the present invention because the halogen, e.g. chlorine, of the silane reacts with the inhibitor, for example as follows:

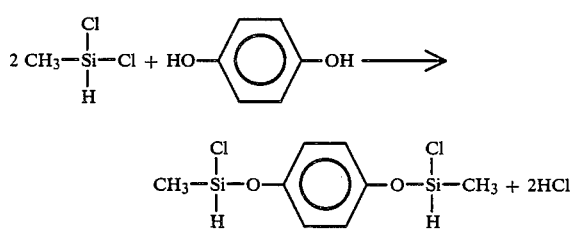

thus there are no OH radicals available for reacting with free radicals to prevent thermal polymerization of the acrylate compound of Formula I.

In view of the foregoing discussion the artisan will be able to determine other suitable inhibitors for use in the process of the present invention without undue experimentation.

Of course, the artisan will appreciate that certain compounds which would suggest themselves as inhibitors for preventing thermal free radical polymerization of the organic acrylate cannot be utilized under certain conditions in practicing the present invention because it will poison the precious metal catalyst. For example, tetramethylthiuram disulfide (TMTDS) would be considered a likely inhibitor for practicing the present invention, however, such compound will poison a platinum or platinum-containing hydrosilation catalyst when the TMTDS-platinum mole ratio is 46 to 1 or higher. The suitability of tetramethylthiuram disulfide for use in combination with other precious metal hydrosilation catalysts can readily be determined without undue experimentation.

Generally the amount of inhibitor compound effective for preventing thermal free radical polymerization of the compound of Formula I is from about 0.01 to about 0.3 percent by weight based on the weight of the compound of Formula I. Of course, more or less can be used without departing from the spirit or intended scope of the invention.

The following examples are provided by way of illustration and not by way of limitation. All parts are by weight unless noted otherwise.

EXAMPLES

Example 1

To a 250 ml three-necked flask equipped with a dropping funnel, dry ice condenser, overhead stirrer, thermometer and heating mantle were added 50.6 grams (0.40 mole) allylmethacrylate, 0.11 gram hydrosilation catalyst prepared in accordance with U.S. Pat. No. 3,814,730 (2.6 weight percent Pt) and 0.08 gram phenothiazine. The contents of the flask were heated to 70° C. and, using the vent of the condenser, purged with nitrogen. When the temperature reached 70° C. the heat source was turned off and 46 grams (0.40 mole) $CH_3SiHCl_2$ was added dropwise. The rate of addition of methyldichlorosilane was adjusted to maintain the reaction temperature between 70° and 80° C. Following completion of the addition of methyldichlorosilane the mixture was heated at 70° C. for thirty minutes and thereafter cooled to 30° C. at which time 0.01 gram triphenyl phosphine was added. The reaction mixture was then stripped at 80° C. and 10 mm Hg for 45 minutes. There was thus obtained 85 grams (80% yield) with 90% purity methacryloxypropylmethyldichlorosilane.

Example 2

To a three-necked flask equipped as in Example 1 there was added 260 grams allylacrylate (2.32 moles), 0.5 grams catalyst prepared in accordance with U.S. Pat. No. 3,814,730 (2.6 weight percent Pt) and 1.04 grams phenothiazine. The mixture was heated with stirring to 65° C. and, using the vent of the condenser, purged with nitrogen. The heat source was then turned off and 237 grams (2.32 moles) $CH_3SiHCl_2$ was added dropwise, the temperature of the reaction mass being maintained at about 70° C. Upon completion of the addition of methyldichlorosilane the crude product was cooled to room temperature. One gram phenothiazine and 0.05 gram triphenyl phosphine were added to the product prior to distillation. Acryloxypropylmethyldichlorosilane (360 grams, 68% yield) was distilled at 109°-112° C./10 mm Hg.

Example 3

To a three-necked flask equipped as in Example 1 there was added 50.6 grams allylmethacrylate (0.40 mole), 0.11 grams catalyst prepared in accordance with U.S. Pat. No. 3,814,730 (2.6 weight percent Pt) and 0.18 grams hydroquinone (1.6 m mole). The mixture was heated with stirring to 75° C. and purged with nitrogen. The heat source was then turned off and 42 grams $CH_3SiHCl_2$ was added dropwise at a rate sufficient to maintain the reaction temperature at 60°-80° C. The contents of the flask gelled after 21 grams of $CH_3SiHCl_2$ had been added.

Example 4

The procedure of Example 3 was repeated except that 0.18 gram phenothiazine (0.9 m mole) was substituted for hydroquinone. After the addition of $CH_3SiHCl_2$ the mixture did not gel and there was obtained 70% yield methacryloxypropylmethyldichlorosilane (based on gas chromatographic analysis).

Example 5

The procedure of Example 3 was repeated except that 0.18 gram phenanthroline (1 m mole) was substituted for hydroquinone. During the addition of $CH_3SiHCl_2$ external heat was supplied as necessary to maintain the reaction temperature between 60° and 80° C. After the addition of $CH_3SiHCl_2$ (3 hours), the mixture was heated with stirring for an additional 12 hours at 60° to 80° C. Gas chromatographic analysis showed that there was obtained a 92% yield of methacryloxypropylmethyldichlorosilane.

Example 6

The procedure of Example 3 was repeated except that 0.18 gram thiazole (2 m mole) was substituted for hydroquinone. After 12 hours of reaction gas chromatographic analysis showed 52% yield. There was then added an additional 0.5 gram catalyst (2.9 percent Pt) and the mixture heated with stirring at 60° C. for 30 minutes. Gas chromatographic analysis showed 84% yield of methacryloxypropylmethyldichlorosilane.

Example 7

The procedure of Example 3 was repeated except that 0.18 gram 2-mercaptobenzothiazole (1 m mole) was substituted for hydroquinone. After 12 hours of reaction gas chromatographic analysis showed 30% yield. There was then added an additional 0.5 grams catalyst (2.9 percent Pt) and the mixture heated with stirring at about 60° C. for two hours. Gas chromatographic analysis showed 96% yield of methacryloxypropylmethyldichorosilane.

I claim:

1. A method for making acrylate-functional halosilanes or halosiloxanes, comprising reacting an organic acrylate and halosilane or halosiloxane having at least one silicon-bonded hydrogen atom in the presence of a hydrosilation catalyst and an amount of inhibitor effective for inhibiting the thermal free radical polymerization of said organic acrylate.

2. The method of claim 1 wherein the organic acrylate has the general formula

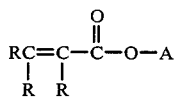

wherein each R is independently selected from the group consisting of hyrogen atoms and monovalent substituted or unsubstituted hydrocarbon radicals having from 1 to 12 carbon atoms, and A is an unsaturated hydrocarbon radical.

3. The method of claim 1 or 2 wherein the halosilane has the general formula

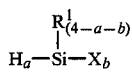

and the halosiloxane has the general formula

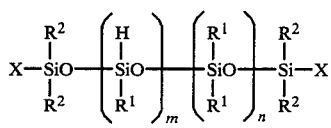

wherein $R^1$ is independently selected from the group consisting of monovalent substituted or unsubstituted hydrocarbon radicals having from 1 to 12 carbon atoms and monovalent substituted or unsubstituted hydrocarbonoxy radicals having from 1 to 12 carbon atoms; $R^2$ is, independently, hydrogen or $R^1$, X is a halogen atom, a equals 1, 2 or 3, b equals 1, 2 or 3, the sum of a and b equals 2 to 4, inclusive, m and n are equal to 0 or a positive integer with the proviso that if m equals zero, at least one $R^2$ is a hydrogen atom.

4. The method of claim 3 wherein the inhibitor is selected from the group consisting of phenothiazine, phenathroline, thiazole, 2-mercaptobenzothiazole, 2,4-dimethylthiazole and 2-benzimidazolethiol.

5. The method of claim 4 wherein the inhibitor is phenothiazine.

6. The method of claim 2 wherein A is selected from the group consisting of vinyl, allyl, methallyl and butenyl.

7. The method of claim 3, wherein X is chlorine.

8. An acrylate-functional halosilane or halosiloxane comprising the reaction product of an organic acrylate and halosilane or halosiloxane having silicon-bonded hydrogen atoms reacted in the presence of a hydrosilation catalyst and an amount of inhibitor effective for inhibiting the thermal free radical polymerization of said organic acrylate.

9. An acrylate-functional halosilane having the general formula

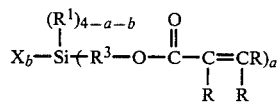

wherein each R is independently selected from the group consisting of hydrogen atoms and monovalent substituted or unsubstituted hydrocarbon radicals having from 1 to 12 carbon atoms; $R^1$ is independently selected from the group consisting of monovalent substituted and unsubstituted hydrocarbon and hydrocarbonoxy radicals having from 1 to 12 carbon atoms, $R^3$ is a divalent saturated hydrocarbon radical, X is a halogen atom, a equals 1, 2 or 3, b equals 1, 2 or 3 and the sum of a and b equals 2 to 4, inclusive.

10. An acrylate-functional halosiloxane having the general formula

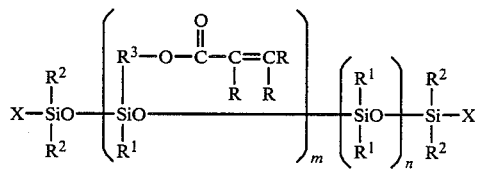

where R is independently selected from the group consisting of hydrogen atoms and monovalent substituted or unsubstituted hydrocarbon radicals having from 1 to 12 carbon atoms, $R^1$ is independently selected from the group consisting of monovalent substituted or unsubstituted hydrocarbon and hydrocarbonoxy radicals having from 1 to 12 carbon atoms, $R^2$ is, independently, hydrogen or an $R^1$ radical, $R^3$ is a saturated divalent hydrocarbon radical, X is a halogen atom, and m and n are equal to 0 or a positive integer with the proviso that if m equals zero, at least one $R^2$ is an

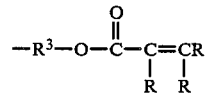

radical.

* * * * *